US009464128B2

(12) United States Patent
Liu et al.

(10) Patent No.: US 9,464,128 B2
(45) Date of Patent: Oct. 11, 2016

(54) SITE-SPECIFIC PEGYLATED LINEAR SALMON CALCITONIN ANALOGUES

(75) Inventors: Keliang Liu, Beijing (CN); Jiankun Qie, Beijing (CN); Zhixia Yang, Beijing (CN); Yuanjun Liang, Beijing (CN); Ying Wang, Beijing (CN); Zehui Gong, Beijing (CN); Huajin Dong, Beijing (CN)

(73) Assignee: INSTITUTE OF PHARMACOLOGY AND TOXICOLOGY ACADEMY OF MILITARY MEDICAL SCIENCES P.L.A., Beijing (CN)

( * ) Notice: Subject to any disclaimer, the term of this patent is extended or adjusted under 35 U.S.C. 154(b) by 795 days.

(21) Appl. No.: 12/664,326

(22) PCT Filed: Jun. 4, 2008

(86) PCT No.: PCT/CN2008/001093
§ 371 (c)(1),
(2), (4) Date: May 17, 2010

(87) PCT Pub. No.: WO2008/151512
PCT Pub. Date: Dec. 18, 2008

(65) Prior Publication Data
US 2010/0227815 A1    Sep. 9, 2010

(30) Foreign Application Priority Data
Jun. 12, 2007    (CN) .......................... 2007 1 0110970

(51) Int. Cl.
C07K 14/585    (2006.01)
A61K 47/48     (2006.01)
A61K 38/00     (2006.01)

(52) U.S. Cl.
CPC ....... *C07K 14/585* (2013.01); *A61K 47/48215* (2013.01); *A61K 38/00* (2013.01)

(58) Field of Classification Search
None
See application file for complete search history.

(56) References Cited

U.S. PATENT DOCUMENTS

| 4,921,697 A * | 5/1990 | Peterlik et al. ............... 424/85.5 |
| 5,364,840 A * | 11/1994 | Basava et al. ............... 514/11.9 |
| 6,482,825 B2 * | 11/2002 | Carpino et al. ............... 514/248 |
| 6,506,730 B1 | 1/2003 | Lee et al. |
| 6,953,791 B2 * | 10/2005 | Carpino et al. .......... 514/213.01 |
| 7,056,882 B2 * | 6/2006 | Kuberasampath et al. ......................... 424/130.1 |
| 2006/0063914 A1* | 3/2006 | Lee et al. ..................... 530/307 |
| 2010/0227815 A1* | 9/2010 | Liu et al. ........................ 514/12 |

FOREIGN PATENT DOCUMENTS

| CN | 1167114 A | 12/1997 |
| CN | 1532206 A | 9/2004 |
| CN | 1532207 A | 9/2004 |
| CN | 1781933 A | 6/2006 |
| EP | 0511903 A2 | 11/1992 |
| JP | 2003-507344 A | 2/2003 |
| WO | 2007054030 A1 | 5/2007 |

OTHER PUBLICATIONS

Yang et al. Synthesis of salmon calcitonin analogs using Fmoc-based chemistry on MBHA resins. Chinese Chemical Letters (1999), 10(7), 549-552. (Abstract).*
Yang et al. Chemical stability of salmon calcitonin (sCT) substitution analogs in aqueous solution. Yaoxue Xuebao (1998), 33(8), 610-615. (Abstract).*
Jiang et al. Amphipathic helical potency and its relationship to the biological activity of synthetic calcitonin derivatives. Peptides: Biology and Chemistry, Proceedings of the Chinese Peptide Symposium, 4th, Chengdu, Peop. Rep. China, Jul. 21-25, 1996 (1998), Meeting Date 1996, 102-103. (Abstract).*
Kang Choon Lee et al., "Isolation, characterization, and stability of Positional Isomers of Mono-PEGylated Salmon Calcitonins", Pharmaceutical Research, 1999, vol. 16, No. 6, pp. 813-818, see p. 813, right column, paragraph I, last paragraph—p. 814, left column, paragraph 2, p. 815, left column, paragraph 4, fig. 1.*
Jin & Tian, "Calcitonin prevents bone loss of castrated male rats," Chinese Journal of Osteoporosis 3, 21-24, 1997.*
Chang et al., "Observation on the effects of salmon calcitonin in intractable pain treatment of 58 patients with advanced malignancy bone metastases," China Pharmaceuticals 12, 64, 2003.*
International Search Report dated Sep. 18, 2008 (PCT/CN2008/001093); ISA/CN.
Chang et al., "Observation on the effects of salmon calcitonin in intractable pain treatment of 58 patients with advanced malignancy bone metastases," China Pharmaceuticals 12, 64, 2003, including English translation of relevant portions.
Jin & Tian, "Calcitonin prevents bone loss of castrated male rats," Chinese Journal of Osteoporosis 3, 21-24, 1997 (English abstract, p. 1).
Yang et al., "Secondary Structure in Solution of an Analog of Salmon Calcitonin: [Val1, Ala7]5CT," Chinese Chemical Letters, vol. 10, No. 7, pp. 555-558, 1999.
Shin et al., "Nasal Absorption and Pharmacokinetic Disposition of Salmon Calcitonin Modified with Low Molecular Weight Polyethylene Glycol," Chemical Pharma Bulletin, vol. 52, No. 8, Aug. 2004, pp. 957-960.
Youn et al., "High-yield production of biologically active mono-PEGylated salmon calcitonin by site-specific PEGylation," Journal of Controlled Release, vol. 117, No. 3, Feb. 2007, pp. 371-379.
Yang et al., "Chemical Stability of Salmon Calcitonin (sCT) Analogues in Aqueous Solution," ACTA Pharmaceutica Sinica, vol. 33, No. 8, 1998, pp. 610-615; English Abstract on pp. 614-615.

(Continued)

*Primary Examiner* — Maury Audet
(74) *Attorney, Agent, or Firm* — Banner & Witcoff, Ltd.

(57) ABSTRACT

The present invention relates to site-specific PEGylated linear salmon calcitonin analogs, or pharmaceutically acceptable salts thereof, process for their preparation, pharmaceutical compositions comprising them, and their use for the preparation of a medicament for the treatment or prevention of diseases associated with bone metabolism, e.g., osteoporosis.

8 Claims, No Drawings

(56) References Cited

OTHER PUBLICATIONS

Veronese and Pasut, "PEGylation, successful approach to drug delivery," Drug Discovery Today, Nov. 2005, vol. 10, No. 21, pp. 1451-1458.

Roberts et al., "Chemistry for peptide and protein PEGylation," Advanced Drug Delivery Reviews, 2002, vol. 54, pp. 459-476.

Extended European Search Report mailed Sep. 29, 2014 for EP Application Serial No. 08757405.9.

Veronese, "Peptide and protein PEGylation: a review of problems and solutions," Biomaterials, 2001, vol. 22, No. 5, pp. 405-417.

* cited by examiner

SEQUENCE LISTING

<160> NUMBER OF SEQ ID NOS: 13

<210> SEQ ID NO 1
<211> LENGTH: 29
<212> TYPE: PRT
<213> ORGANISM: Artificial Sequence
<220> FEATURE:
<223> OTHER INFORMATION: synthetic construct
<221> NAME/KEY: VARIANT
<222> LOCATION: (1)...(1)
<223> OTHER INFORMATION: Xaa = C, Acm-C, N-alpha-propinol-C, A, D-Ala,
      V, L, I, G, S, T, F, M, W
<221> NAME/KEY: VARIANT
<222> LOCATION: (7)...(7)
<223> OTHER INFORMATION: Xaa = C, Acm-C, A, D-A, V, L, I, G, S, T, F,
      M, or W
<221> NAME/KEY: VARIANT
<222> LOCATION: (8)...(8)
<223> OTHER INFORMATION: Xaa = V, G, M, L, I, C, A, or D-A
<221> NAME/KEY: VARIANT
<222> LOCATION: (11)...(11)
<223> OTHER INFORMATION: Xaa = K, C, R, or Q
<221> NAME/KEY: VARIANT
<222> LOCATION: (16)...(16)
<223> OTHER INFORMATION: Xaa = L, A, D-A, I, C, V, or G
<221> NAME/KEY: VARIANT
<222> LOCATION: (17)...(17)
<223> OTHER INFORMATION: Xaa = H, C, K, or R
<221> NAME/KEY: VARIANT
<222> LOCATION: (18)...(18)
<223> OTHER INFORMATION: Xaa = K, R, C, H, or Q
<221> NAME/KEY: VARIANT
<222> LOCATION: (19)...(19)
<223> OTHER INFORMATION: Xaa = LGTY, QTY, TY, LQT, LQ, CY, L, Y, A, D-A,
      C or is absent
<221> NAME/KEY: VARIANT
<222> LOCATION: (21)...(21)
<223> OTHER INFORMATION: Xaa = R, K, H, or C
<221> NAME/KEY: VARIANT
<222> LOCATION: (27)...(27)
<223> OTHER INFORMATION: Xaa = A or D-A

<400> SEQUENCE: 1

Xaa Ser Asn Leu Ser Thr Xaa Xaa Leu Gly Xaa Leu Ser Gln Glu Xaa
 1               5                  10                  15

Xaa Xaa Xaa Pro Xaa Thr Asn Thr Gly Ser Xaa Thr Pro
            20                  25

<210> SEQ ID NO 2
<211> LENGTH: 32
<212> TYPE: PRT
<213> ORGANISM: Artificial Sequence
<220> FEATURE:
<223> OTHER INFORMATION: synthetic construct

<400> SEQUENCE: 2

Ala Ser Asn Leu Ser Thr Cys Val Leu Gly Lys Leu Ser Gln Glu Leu
 1               5                  10                  15

His Lys Leu Gln Thr Tyr Pro Arg Thr Asn Thr Gly Ser Ala Thr Pro
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: synthetic construct

<400> SEQUENCE: 3

Val Ser Asn Leu Ser Thr Cys Val Leu Gly Lys Leu Ser Gln Glu Leu
 1               5                  10                  15

```
His Lys Gln Thr Tyr Pro Arg Thr Asn Thr Gly Ser Ala Thr Pro
            20                  25                  30

<210> SEQ ID NO 4
<211> LENGTH: 28
<212> TYPE: PRT
<213> ORGANISM: Artificial Sequence
<220> FEATURE:
<223> OTHER INFORMATION: synthetic construct

<400> SEQUENCE: 4

Val Ser Asn Leu Ser Thr Ala Val Leu Gly Lys Leu Ser Gln Glu Cys
1               5                   10                  15

His Lys Pro Arg Thr Asn Thr Gly Ser Ala Thr Pro
            20                  25

<210> SEQ ID NO 5
<211> LENGTH: 28
<212> TYPE: PRT
<213> ORGANISM: Artificial Sequence
<220> FEATURE:
<223> OTHER INFORMATION: synthetic construct

<400> SEQUENCE: 5

Val Ser Asn Leu Ser Thr Ala Val Leu Gly Gln Leu Ser Gln Glu Cys
1               5                   10                  15

His Gln Pro Arg Thr Asn Thr Gly Ser Ala Thr Pro
            20                  25

<210> SEQ ID NO 6
<211> LENGTH: 28
<212> TYPE: PRT
<213> ORGANISM: Artificial Sequence
<220> FEATURE:
<223> OTHER INFORMATION: synthetic construct

<400> SEQUENCE: 6

Val Ser Asn Leu Ser Thr Cys Val Leu Gly Lys Leu Ser Gln Glu Leu
1               5                   10                  15

His Lys Pro Arg Thr Asn Thr Gly Ser Ala Thr Pro
            20                  25

<210> SEQ ID NO 7
<211> LENGTH: 31
<212> TYPE: PRT
<213> ORGANISM: Artificial Sequence
<220> FEATURE:
<223> OTHER INFORMATION: synthetic construct

<400> SEQUENCE: 7

Val Ser Asn Leu Ser Thr Cys Val Leu Gly Lys Leu Ser Gln Glu Leu
1               5                   10                  15

His Lys Gln Thr Tyr Pro Arg Thr Asn Thr Gly Ser Ala Thr Pro
            20                  25                  30

<210> SEQ ID NO 8
<211> LENGTH: 28
<212> TYPE: PRT
<213> ORGANISM: Artificial Sequence
<220> FEATURE:
<223> OTHER INFORMATION: synthetic construct

<400> SEQUENCE: 8

Val Ser Asn Leu Ser Thr Cys Val Leu Gly Lys Leu Ser Gln Glu Leu
```

```
                1               5                   10                  15
His Gln Pro Arg Thr Asn Thr Gly Ser Ala Thr Pro
            20                  25

<210> SEQ ID NO 9
<211> LENGTH: 28
<212> TYPE: PRT
<213> ORGANISM: Artificial Sequence
<220> FEATURE:
<223> OTHER INFORMATION: synthetic construct

<400> SEQUENCE: 9

Val Ser Asn Leu Ser Thr Cys Val Leu Gly Gln Leu Ser Gln Glu Leu
1               5                   10                  15

His Lys Pro Arg Thr Asn Thr Gly Ser Ala Thr Pro
            20                  25

<210> SEQ ID NO 10
<211> LENGTH: 28
<212> TYPE: PRT
<213> ORGANISM: Artificial Sequence
<220> FEATURE:
<223> OTHER INFORMATION: synthetic construct

<400> SEQUENCE: 10

Val Ser Asn Leu Ser Thr Cys Val Leu Gly Gln Leu Ser Gln Glu Leu
1               5                   10                  15

His Gln Pro Arg Thr Asn Thr Gly Ser Ala Thr Pro
            20                  25

<210> SEQ ID NO 11
<211> LENGTH: 29
<212> TYPE: PRT
<213> ORGANISM: Artificial Sequence
<220> FEATURE:
<223> OTHER INFORMATION: synthetic construct

<400> SEQUENCE: 11

Val Ser Asn Leu Ser Thr Ala Val Leu Gly Lys Leu Ser Gln Glu Leu
1               5                   10                  15

His Lys Cys Pro Arg Thr Asn Thr Gly Ser Ala Thr Pro
            20                  25

<210> SEQ ID NO 12
<211> LENGTH: 30
<212> TYPE: PRT
<213> ORGANISM: Artificial Sequence
<220> FEATURE:
<223> OTHER INFORMATION: synthetic construct

<400> SEQUENCE: 12

Val Ser Asn Leu Ser Thr Ala Val Leu Gly Lys Leu Ser Gln Glu Leu
1               5                   10                  15

His Lys Cys Tyr Pro Arg Thr Asn Thr Gly Ser Ala Thr Pro
            20                  25                  30

<210> SEQ ID NO 13
<211> LENGTH: 4
<212> TYPE: PRT
<213> ORGANISM: Artificial Sequence
<220> FEATURE:
<223> OTHER INFORMATION: peptide
```

<400> SEQUENCE: 13

Leu Gln Thr Tyr
1

SITE-SPECIFIC PEGYLATED LINEAR SALMON CALCITONIN ANALOGUES

This application incorporates by reference the contents of a 5.3 kb text file created on Jul. 16, 2015 and named "20150716_12664326substitutesequencelisting.txt" which is the sequence listing for this application.

TECHNICAL FIELD

The present invention relates to site-specific PEGylated linear salmon calcitonin analogues, process for their preparation, pharmaceutical compositions comprising them, and their use for the treatment of diseases associated with bone metabolism, e.g., osteoporosis and bone pain.

BACKGROUND ART

Calcitonin is secreted by thyroid parafollicular cells (C cells) of mammals or by post-branchial body of vertebrates such as fishes and birds. It is a type of single-strand polypeptide compound containing 32 amino acid residues, and is one of important hormones to maintain calcium-phosphorus metabolism in vivo. It mainly takes the action of inhibiting bone absorption, and reducing blood calcium level. Although natural calcitonins isolated from different genera are somewhat different in terms of components of amino acid residues, all of them include in their molecules the following structural features: a dithio ring structure formed by cysteines at 1,7-positions of N-terminal and a proline amide group at C-terminal. Natural calcitonin as secreted by vertebrates such as fishes exhibits the highest activity, while that as secreted by mammals exhibits a relatively low activity, for example, the activity of salmon calcitonin (sCT, which first order sequence is:
H-cyclo-($Cys^1$-Ser-Asn-Leu-$Ser^5$-Thr-$Cys^7$)-Val-Leu-Gly-$Lys^{11}$-Leu-Ser-Gln-Glu-$Leu^{16}$-His-Lys-Leu-Gln-$Thr^{21}$-Tyr-Pro-Arg-Thr-$Asn^{26}$-Thr-Gly-Ser-$Gly^{30}$-$Thr^{31}$-Pro-$NH_2$) is 30 times greater than that of human calcitonin (hCT). Calcitonin can effectively prevent osteoporosis, and can simultaneously alleviate the symptoms such as bone pain and anergy of the patients suffering from osteoporosis. At present, the synthetic analogues of sCT, hCT and eel calcitonin (eCT) are mainly used in clinic for the treatment of senile osteoporosis, postmenopausal osteoporosis, Paget's disease, hypercalcemia and bone pain caused by osteoporosis or bone tumor.

sCT, as developed by Sandoz Co., was mainly used for the treatment of osteoporosis of postmenopausal women and etc., and was also suitable for patients with estrogen contraindications and male patients suffering from osteoporosis, and its injection had already been marketed in USA in 1986, with trade name Miacalcic, and a conventional dose of 10-20 μg/day. sCT could activate adenylate cyclase (cAMP). It was demonstrated by study that cAMP, as one important second messenger in osteoclasts, participated in the inhibitory action on osteoclasts. sCT could also act on human osteoblasts, to simulate the proliferation and differentiation of osteoblasts. The action of sCT of reducing calcium and phosphorus levels in blood was mainly effectuated by inhibiting the transformation of bone calcium to blood calcium. At the same time, sCT could also promote the excretion of calcium and phosphorus in urine and bile, and inhibit the absorption of calcium and phosphorus ions in digestive tract. In addition, sCT could also specifically bind with calcitonin receptor in cerebrum and hypothalamus, and mediate central analgesic effect.

However, natural sCT can be easily inactivated by enzymolysis in vivo, and has a relatively short action time, which therefore shall be administered parenterally. Natural sCT also has a relatively poor stability in solution as well as with enzyme, and this, someone thinks, may be relevant to its dithio ring. Thus, in clinic, natural sCT shall be administered by injection frequently for a long period of time in order to achieve the treatment effectiveness, which thereby results in a poor compliance of the patients with medical treatment, and a reduction in treatment quality. Moreover, due to the presence of dithio ring, the synthesis of calcitonin is relatively difficult, and the cost thereof is increased, so that the drug obtained is too expensive to accept by the patients.

It was proved by experiment that dithio ring took different actions with respect to the activity of different calcitonins Dithio ring in sCT was not an essential group for its activity, and the linear analogue, i.e., sCT analogue free of 1,7-dithio ring, could still retain a preferable bioactivity. The synthesis of linear salmon calcitonin analogue (hereinafter referred to as sCT(L)) would become less difficult, and the cost thereof would be reduced. In addition, it was demonstrated by study that polypeptide drugs, after PEGylated, could still retain a good bioactivity, and could have a notably prolonged half life in organism. At present, the PEGylation of sCT has already been reported. It was discovered, by studying the metabolism in kidney homogenate, that the metabolic half life of the products PEGylated at three sites was far higher than that of sCT (4.8 min), i.e., the metabolic half life of the product PEGylated at N-terminal was 125.5 min, that of the product PEGylated at $Lys^{11}$ was 157.3 min, and that of the product PEGylated at $Lys^{18}$ was 281.5 min (K C Lee, et al, Pharm. Res., 1999, 16:813-818). In addition, the site-specific PEGylation of sCT at 8-amino of $Lys^{18}$ was also reported (Y S Youn, et al, Pharm. Dev. Technol., 2005, 10(3): 389-396; J Controlled Release, 2006, 114(3): 334-342; 2007, 117(3): 371-379).

Then, by virtue of the characteristics of PEG capable of prolonging the action time, increasing the bioavailability and etc. of peptide drugs, it is possible to carry out an exact site-specific mono-PEGylation of linear sCT analogues using a reaction-specific chemical modification process. Therefore, linear sCT analogues shall include, or to which shall be re-introduced, an amino acid residue comprising a reaction-specific functional group, to increase the specificity of the reaction. The preparation of the linear sCT analogues may be implemented by using any conventional technique in the art, preferably a chemical synthetic process.

The object of the present invention is to provide a type of PEGylated sCT(L) analogues, which is in favor of developing long-acting medicaments and preparations for the treatment of bone diseases, e.g., osteoporosis.

CONTENTS OF THE INVENTION

The abbreviations used in the present invention have the following meanings:
sCT—salmon calcitonin
PEG—polyethylene glycol
Ala—alanine
Arg—arginine
Asn—asparagine
Cys—cysteine
Gln—glutamine
Glu—glutamic acid
Gly—glycine
His—histidine
Leu—leucine Lys—lysine
Pro—proline
Ser—serine
Thr—threonine
Tyr—tyrosine
Val—valine
Fmoc—fluorenylmethyloxycarbonyl
DMF—dimethylformamide
DCC—Dicyclohexylcarbodiimide
HBTU—2-(1H-1-hydroxybenzotriazole)-1,1,3,3-tetramethyl-uronium-hexafluorophosphate
HOBt—1-hydroxybenzotriazole
TFA—trifluoroacetic acid
EDT—mercaptoethanol
RP-HPLC—reversed phase-high performance liquid chromatography One object of the present invention is to provide site-specific PEGylated linear salmon calcitonin analogues, which is obtained by changing certain amino acid residues in the amino acid sequence of the linear salmon calcitonin analogues to remain only one amino, carboxyl or mercapto group on the side chain, and carrying out a site-specific PEGylation on said amino, carboxyl or mercapto group. The site-specific PEGylated linear salmon calcitonin analogues of the invention have the structures of the formula (I), formula (II) or formula (III) as given and defined below.

Another object of the present invention is to provide a process for preparing the site-specific PEGylated linear salmon calcitonin analogues.

The present invention further relates to a pharmaceutical composition comprising at least one type of the site-specific PEGylated linear salmon calcitonin analogues, or a stereoisomer or a pharmaceutically acceptable salt thereof, and pharmaceutically acceptable vehicles or excipients.

The present invention still further relates to use of the site-specific PEGylated linear salmon calcitonin analogues for the preparation of a medicament for the treatment and prevention of diseases or symptoms associated with bone metabolism, e.g., osteoporosis and bone pain.

The site-specific PEGylated linear salmon calcitonin analogues of the invention have the structure of formula (I):

PEG-M-Cys-sCT(L)   (I)

wherein,
PEG is RO(CH$_2$CH$_2$O)$_n$—CH$_2$CH$_2$—, R=H or CH$_3$, n=25-2500;

M = 
$$\begin{array}{c} \text{pyrrolidine-2,5-dione (N-linked)} \end{array}$$ or $-S(=O)_2-CH_2-CH_2-$ or $-NH-C(=O)-CH_2-CH_3$ ;

Cys is cysteine, which may lie in any site of the linear salmon calcitonin analogues, including N-terminal, C-terminal and any site in the sequence;

sCT(L) is linear salmon calcitonin peptide analogue, having the following structural features:

(SEQ ID NO: 1)
Aa$_1$-Ser-Asn-Leu-Ser-Thr-Aa$_2$-Aa$_3$-Leu-Gly-Aa$_4$-Leu-

Ser-Gln-Glu-Aa$_5$-Aa$_6$-Aa$_7$-Aa$_8$-Pro-Aa$_9$-Thr-Asn-Thr-

Gly-Ser-Aa$_{10}$-Thr-Pro-NH$_2$ wherein,
Aa$_1$ is a non-polar amino acid selected from Cys, Acm-Cys, N-α-propinol-Cys, Ala, D-Ala, Val, Leu, Ile, Gly, Ser, Thr, Phe, Met, Trp;
Aa$_2$ is a non-polar amino acid selected from Cys, Acm-Cys, Ala, D-Ala, Val, Leu, Ile, Gly, Ser, Thr, Phe, Met, Tip, and Aa$_1$ and Aa$_2$ are not both Cys;
Aa$_3$ is a non-polar amino acid selected from Val, Gly, Met, Leu, Ile, Cys, Ala, D-Ala;
Aa$_4$ is an amino acid selected from Lys, Cys, Arg, Gln;
Aa$_5$ is an amino acid selected from Leu, Ala, D-Ala, Ile, Cys, Val, Gly;
Aa$_6$ is an amino acid selected from His, Cys, Lys, Arg;
Aa$_7$ is an amino acid selected from Lys, Arg, Cys, His, Gln;
Aa$_8$ is selected from -Leu-Gln-Thr-Tyr- (SEQ ID NO:13), -Gln-Thr-Tyr-, -Thr-Tyr-, -Leu-Gln-Thr-, -Leu-Gln-, -Cys-Tyr-, Leu, Tyr, Ala, D-Ala, Cys;
Aa$_9$ is an amino acid selected from Arg, Lys, His, Cys;
Aa$_{10}$ is an amino acid selected from Gly, Ala, D-Ala, Cys, Pro, D-Pro.
Unless especially specified, all of the amino acids are L-amino acids.

According to one preferred embodiment of the present invention, the sCT(L) in the formula (I) has the following structural features:
Aa$_1$ is Cys, Ala, D-Ala, Val;
Aa$_2$ is Cys, Ala, D-Ala, and Aa$_1$ and Aa$_2$ are not both Cys;
Aa$_3$ is Val, Gly, Ala, D-Ala;
Aa$_4$ is Lys, Arg;
Aa$_5$ is Leu, Ala, D-Ala, Cys;
Aa$_6$ is His, Arg;
Aa$_7$ is Lys, Arg;
Aa$_8$ is -Leu-Gln-Thr-Tyr-, -Ala-Gln-Thr-Tyr-;
Aa$_9$ is Arg, His;
Aa$_{10}$ is Gly, Ala, D-Ala.
Unless especially specified, all of the amino acids are L-amino acids.

According to one further preferred embodiment of the present invention, the sCT(L) in the formula (I) has the following structural features:
Aa$_1$ is D-Ala, Val;
Aa$_2$ is Cys;
Aa$_3$ is Val, Gly;
Aa$_4$ is Lys;
Aa$_5$ is Leu, Ala;
Aa$_6$ is His;
Aa$_7$ is Lys;
Aa$_8$ is -Leu-Gln-Thr-Tyr-;
Aa$_9$ is Arg;
Aa$_{10}$ is Ala, D-Ala.
Unless especially specified, all of the amino acids are L-amino acids.

The site-specific PEGylated linear salmon calcitonin analogues of the invention may also have the structure of formula (II):

[PEG-X—(CH$_2$)$_m$CO—NH]$_z$-Cys-sCT(L)   (II)

wherein,
PEG is RO(CH$_2$CH$_2$O)$_n$—CH$_2$CH$_2$—, R=H or CH$_3$, n=25-2500;
X=O, NH or NHCO;
m=0-6;
z=1;
Cys is cysteine, which may lie in any site of the linear salmon calcitonin analogues, including N-terminal, C-terminal and any site in the sequence;
sCT(L) is linear salmon calcitonin peptide analogue, the definition and preferred embodiments of which are the same as those described with formula (I).

The site-specific PEGylated sCT(L) linear salmon calcitonin analogues of formula (II) are obtained by covalently binding reaction of a PEGylating agent having carboxyl active group, aldehyde group, isocyano group, isothiocyano group and the like with terminal amino group, lysine amino group, histidine amino group or other amino group as introduced in sCT(L).

The site-specific PEGylated linear salmon calcitonin analogues of the present invention may also have the structure of formula (III):

Cys-sCT(L)-[CO—X-PEG]$_z$     (III)

wherein,
PEG is RO(CH$_2$CH$_2$O)$_n$—CH$_2$CH$_2$—, R=H or CH$_3$, n=25-2500;
X=O, NH or NHCO;
z=1;
Cys is cysteine, which may lie in any site of the linear salmon calcitonin analogues, including N-terminal, C-terminal and any site in the sequence;
sCT(L) is linear salmon calcitonin peptide analogue, the definition and preferred embodiments of which are the same as those described with formula (I).

The site-specific PEGylated linear salmon calcitonin analogues of formula (III) are obtained by covalently binding reaction of a PEGylating agent having carboxyl active group, amino group and the like with terminal carboxyl group, aspartic acid carboxyl group, glutamic acid carboxyl group or other carboxyl group as introduced in sCT(L).

The site-specific PEGylated linear salmon calcitonin analogues further include the compounds obtained by replacing any amino acid residue in the linear amino acid sequence with cysteine and then modifying with mPEG-MAL, PEG-VS or PEG-IODO.

According to the present invention, the following linear salmon calcitonin analogues capable of site-specific PEGylation are preferred:

(1) [D-Ala$^1$, Cys$^7$, D-Ala$^{30}$]sCT;     D-Ala-Ser-Asn-Leu-Ser-Thr-Cys-Val-Leu-Gly-Lys-Leu-Ser-Gln-Glu-Leu-His-Lys-Leu-Gln-Thr-Tyr-Pro-Arg-Thr-Asn-Thr-Gly-Ser-D-Ala-Thr-Pro (SEQ ID NO: 2)

(2) [Val$^1$, Cys$^7$, Des-19, Ala$^{30}$]sCT;     Val-Ser-Asn-Leu-Ser-Thr-Cys-Val-Leu-Gly-Lys-Leu-Ser-Gln-Glu-Leu-His-Lys-Gln-Thr-Tyr-Pro-Arg-Thr-Asn-Thr-Gly-Ser-Ala-Thr-Pro (SEQ ID NO: 3)

(3) [Val$^1$, Ala$^7$, Cys$^{16}$, Ala$^{30}$, Des-19-22]sCT;     Val-Ser-Asn-Leu-Ser-Thr-Ala-Val-Leu-Gly-Lys-Leu-Ser-Gln-Glu-Cys-His-Lys-Pro-Arg-Thr-Asn-Thr-Gly-Ser-Ala-Thr-Pro (SEQ ID NO: 4)

(4) [Val$^1$, Ala$^7$, Gln$^{11,18}$, Cys$^{16}$, Ala$^{30}$, Des-19-22]sCT;     Val-Ser-Asn-Leu-Ser-Thr-Ala-Val-Leu-Gly-Gln-Leu-Ser-Gln-Glu-Cys-His-Gln-Pro-Arg-Thr-Asn-Thr-Gly-Ser-Ala-Thr-Pro (SEQ ID NO: 5)

(5) [Val$^1$, Cys$^7$, Des-19-22, Ala$^{30}$]sCT;     Val-Ser-Asn-Leu-Ser-Thr-Cys-Val-Leu-Gly-Lys-Leu-Ser-Gln-Glu-Leu-His-Lys-Pro-Arg-Thr-Asn-Thr-Gly-Ser-Ala-Thr-Pro (SEQ ID NO: 6)

(6) [Val$^1$, Cys$^7$, Ala$^{30}$, Des-19]sCT;     Val-Ser-Asn-Leu-Ser-Thr-Cys-Val-Leu-Gly-Lys-Leu-Ser-Gln-Glu-Leu-His-Lys-Gln-Thr-Tyr-Pro-Arg-Thr-Asn-Thr-Gly-Ser-Ala-Thr-Pro (SEQ ID NO: 7)

(7) [Val$^1$, Cys$^7$, Gln$^{18}$, Ala$^{30}$, Des-19-22]sCT;     Val-Ser-Asn-Leu-Ser-Thr-Cys-Val-Leu-Gly-Lys-Leu-Ser-Gln-Glu-Leu-His-Gln-Pro-Arg-Thr-Asn-Thr-Gly-Ser-Ala-Thr-Pro (SEQ ID NO: 8)

(8) [Val$^1$, Cys$^7$, Gln$^{11}$, Ala$^{30}$, Des-19-22]sCT;     Val-Ser-Asn-Leu-Ser-Thr-Cys-Val-Leu-Gly-Gln-Leu-Ser-Gln-Glu-Leu-His-Lys-Pro-Arg-Thr-Asn-Thr-Gly-Ser-Ala-Thr-Pro (SEQ ID NO: 9)

-continued (9) [Val¹, Cys⁷, Gln¹¹,¹⁸, Ala³⁰, Des-19-22]sCT;  
Val-Ser-Asn-Leu-Ser-Thr-Cys-Val-Leu-Gly-Gln-Leu-Ser-Gln-Glu-Leu-His-Gln-Pro-Arg-Thr-Asn-Thr-Gly-Ser-Ala-Thr-Pro (SEQ ID NO: 10)

(10) [Val¹, Ala⁷, Cys¹⁹, Ala³⁰, Des-20-22]sCT;  
Val-Ser-Asn-Leu-Ser-Thr-Ala-Val-Leu-Gly-Lys-Leu-Ser-Gln-Glu-Leu-His-Lys-Cys-Pro-Arg-Thr-Asn-Thr-Gly-Ser-Ala-Thr-Pro (SEQ ID NO: 11)

(11) [Val¹, Ala⁷, Cys¹⁹, Ala³⁰, Des-20-21]sCT.  
Val-Ser-Asn-Leu-Ser-Thr-Ala-Val-Leu-Gly-Lys-Leu-Ser-Gln-Glu-Leu-His-Lys-Cys-Tyr-Pro-Arg-Thr-Asn-Thr-Gly-Ser-Ala-Thr-Pro (SEQ ID NO: 12)

According to the present invention, the following site-specific PEGylated linear salmon calcitonin analogues are preferred:

1 [D-Ala¹, Cys⁷(mPEG$_{5000}$-MAL), D-Ala³⁰]sCT;  
D-Ala-Ser-Asn-Leu-Ser-Thr-Cys(mPEG$_{5000}$-MAL)-Val-Leu-Gly-Lys-Leu-Ser-Gln-Glu-Leu-His-Lys-Leu-Gln-Thr-Tyr-Pro-Arg-Thr-Asn-Thr-Gly-Ser-D-Ala-Thr-Pro (SEQ ID NO: 2)

2 [Val¹, Cys⁷(mPEG$_{5000}$-MAL), Des-19, Ala³⁰]sCT;  
Val-Ser-Asn-Leu-Ser-Thr-Cys(mPEG$_{5000}$-MAL)-Val-Leu-Gly-Lys-Leu-Ser-Gln-Glu-Leu-His-Lys-Gln-Thr-Tyr-Pro-Arg-Thr-Asn-Thr-Gly-Ser-Ala-Thr-Pro (SEQ ID NO: 3)

3 [Val¹, Ala⁷, Cys¹⁶(mPEG$_{5000}$-MAL), Des-19-22, Ala³⁰]sCT;  
Val-Ser-Asn-Leu-Ser-Thr-Ala-Val-Leu-Gly-Lys-Leu-Ser-Gln-Glu-Cys(mPEG$_{5000}$-MAL)-His-Lys-Pro-Arg-Thr-Asn-Thr-Gly-Ser-Ala-Thr-Pro (SEQ ID NO: 4)

4 [Val¹, Ala⁷, Gln¹¹,¹⁸, Cys¹⁶(mPEG$_{5000}$-MAL), Des-19-22, Ala³⁰]sCT;  
Val-Ser-Asn-Leu-Ser-Thr-Ala-Val-Leu-Gly-Gln-Leu-Ser-Gln-Glu-Cys(mPEG$_{5000}$-MAL)-His-Gln-Pro-Arg-Thr-Asn-Thr-Gly-Ser-Ala-Thr-Pro (SEQ ID NO: 5)

5 [Val¹, Cys⁷(mPEG$_{5000}$-MAL), Des-19-22, Ala³⁰]sCT;  
Val-Ser-Asn-Leu-Ser-Thr-Cys(mPEG$_{5000}$-MAL)-Val-Leu-Gly-Lys-Leu-Ser-Gln-Glu-Leu-His-Lys-Pro-Arg-Thr-Asn-Thr-Gly-Ser-Ala-Thr-Pro (SEQ ID NO: 6)

6 [Val¹, Cys⁷(mPEG$_{5000}$-MAL), Des-19, Ala³⁰]sCT;  
Val-Ser-Asn-Leu-Ser-Thr-Cys(mPEG$_{5000}$-MAL)-Val-Leu-Gly-Lys-Leu-Ser-Gln-Glu-Leu-His-Lys-Gln-Thr-Tyr-Pro-Arg-Thr-Asn-Thr-Gly-Ser-Ala-Thr-Pro (SEQ ID NO: 7)

7 [Val¹, Cys⁷(mPEG$_{5000}$-MAL), Gln¹⁸, Des-19-22, Ala³⁰]sCT;  
Val-Ser-Asn-Leu-Ser-Thr-Cys(mPEG$_{5000}$-MAL)-Val-Leu-Gly-Lys-Leu-Ser-Gln-Glu-Leu-His-Gln-Pro-Arg-Thr-Asn-Thr-Gly-Ser-Ala-Thr-Pro (SEQ ID NO: 8)

8 [Val¹, Cys⁷(mPEG$_{5000}$-MAL), Gln¹¹, Des-19-22, Ala³⁰]sCT;  
Val-Ser-Asn-Leu-Ser-Thr-Cys(mPEG$_{5000}$-MAL)-Val-Leu-Gly-Gln-Leu-Ser-Gln-Glu-Leu-His-Lys-Pro-Arg-Thr-Asn-Thr-Gly-Ser-Ala-Thr-Pro (SEQ ID NO: 9)

9 [Val¹, Cys⁷(mPEG$_{5000}$-MAL), Gln¹¹,¹⁸, Des-19-22, Ala³⁰]sCT;  
Val-Ser-Asn-Leu-Ser-Thr-Cys(mPEG$_{5000}$-MAL)-Val-Leu-Gly-Gln-Leu-Ser-Gln-Glu-Leu-His-Gln-Pro-Arg-Thr-Asn-Thr-Gly-Ser-Ala-Thr-Pro (SEQ ID NO: 10)

10 [Val¹, Ala⁷, Cys¹⁹(mPEG$_{5000}$-MAL), Des-20-22, Ala³⁰]sCT; and  
Val-Ser-Asn-Leu-Ser-Thr-Ala-Val-Leu-Gly-Lys-Leu-Ser-Gln-Glu-Leu-His-Lys-Cys(mPEG$_{5000}$-MAL)-Pro-Arg-Thr-Asn-Thr-Gly-Ser-Ala-Thr-Pro (SEQ ID NO: 11)

11 [Val¹, Ala⁷, Cys¹⁹(mPEG$_{5000}$-MAL), Des-20-21, Ala³⁰]sCT.  
Val-Ser-Asn-Leu-Ser-Thr-Ala-Val-Leu-Gly-Lys-Leu-Ser-Gln-Glu-Leu-His-Lys-Cys(mPEG$_{5000}$-MAL)-Tyr-Pro-Arg-Thr-Asn-Thr-Gly-Ser-Ala-Thr-Pro (SEQ ID NO: 12)

The compounds of the present invention are prepared by using conventional polypeptide synthetic processes, including solid-phase polypeptide synthetic process, liquid-phase polypeptide synthetic process and solid-liquid phase polypeptide synthetic process, wherein amino acid is protected by Fmoc-/tBu- or Boc-/Bzl-, and the linking mode includes linking N-terminal to C-terminal in sequence, or firstly synthesizing fragments and then linking the fragments. In the solid-phase synthetic process, various resins (e.g., MBHA, PAL, Rink amide resin, and etc.) capable of forming amide terminal are used as the support, various common condensing agents (e.g., DCC/HOBT, BOP/DIEA, HBTU/HOBt, TBTU, and etc.) are used for carrying out the condensation reaction, then, after completion of the reaction, trifluoroacetic acid or anhydrous HF is used for splitting the polypeptide obtained from the resin. The linking of the polypeptide with a PEGylating agent is carried out in an aqueous solution or a phosphate buffer solution, while appropriately controlling pH of the reaction solution, and monitoring the PEGylated product by RP-HPLC, and then the final product is separated and purified, and determined by MALDI-TOF-MS.

A part of preferred compounds according to the present invention are relatively effective for reducing blood calcium level of animals, and simultaneously exhibit a long-acting performance in preliminary activity study in vivo in animals.

The present invention further relates to a pharmaceutical composition comprising as active ingredient an effective amount of at least one PEGylated polypeptide and/or its stereoisomer or its physiologically nontoxic salt, and pharmaceutically acceptable vehicles or excipients. The term "pharmaceutically acceptable vehicles or excipients" used herein includes any one or all solvents, dispersing mediums, coatings, antibacterial agents or antifungal agents, isotonizing and sustained release agents, and similar physiologically compatible preparations, which are preferably suitable for administration by intravenous injection, intramscular injection, subcutaneous injection, or other parenteral routes. According to the administration route, the active compound may be coated to protect it from inactivation under the influence of acid or other natural conditions.

The term "physiologically nontoxic salt" used herein refers to salts capable of retaining the expected physiological activity of the parent compound while producing no unexpected toxic side-effect, or compositions comprising them, for example, hydrochlorides, hydrobromides, sulfates, phosphates, nitrates, and acetates, oxalates, tartrates, succinates, malates, benzoates, pamoates, alginates, mesylates, napsylates, and etc. According to the cations contained, the salts may also be divided into: inorganic salts such as potassium salts, lithium salts, zinc salts, copper salts, barium salts, bismuth salts, calcium salts, and organic salts such as trialkylammonium salts.

The PEGylated polypeptide compound and its stereoisomer or the pharmaceutical composition comprising it of the invention may be administered in any known route, e.g., orally, intramuscularly, subcutaneously, nasally, and etc. The administration dosage form includes tablets, capsules, buccal tablets, chewable tablets, elixirs, suspensions, transdermal agents, microencapsulated agents, implants, syrups, and etc. It may be common preparations, sustained release preparations, controlled release preparations and various particulate delivery systems. In order to prepare a unit dosage form into a tablet, various biodegradable or biocompatible vehicles as well-known in the art can be widely used. The examples of the vehicle include saline and various buffer aqueous solutions, ethanol or other polyols, liposomes, polylactic acid, vinyl acetate, polyanhdyrides, polyglycolic acid, collagen, poly(ortho ester), and etc.

The administration dose of the PEGylated polypeptide compound of the invention depends on various factors, such as nature and degree of severity of the disease to be prevented or treated; gender, age, body weight, sensitivity and individual reaction of the patient or animal; specific compound used; administration route; administration frequency and treatment effectiveness as expected to be achieved, and etc. The above dose may be administered in the form of a single dose or in the form of several doses, e.g., two, three, four doses.

MODE OF CARRYING OUT THE INVENTION

The following examples and biological active experiments are used to further illustrate the present invention, but shall not be understood to limit the present invention in any manner.

MBHA resin and PAM resin used as support for solid-phase synthesis in the examples are manufactured by Tianjin Nankai Synthesis Co., Ltd.; DCC, HOBT, BOP, DIEA and Fmoc-protected natural amino acids are manufactured by GL Biochem (Shanghai) Ltd. and Suzhou Tianma New Technology Co., Ltd.

EXAMPLE 1

Synthesis of [D-Ala$^1$,Cys$^7$(mPEG$_{5000}$-MAL),D-Ala$^{30}$]sCT (Compound 12)

Step 1: Solid-phase synthesis of [D-Ala$^1$,Cys$^7$,D-Ala$^{30}$] sCT (Compound 1)

Using 250 mg MBHA resin (0.12 mmol) as solid-phase support, Fmoc-Pro-OH, Fmoc-Thr(tBu)-OH, Fmoc-D-Ala-OH, Fmoc-Ser(tBu)-OH, Fmoc-Gly-OH, Fmoc-Asn(Trt)-OH, Fmoc-Arg(Pbf)-OH, Fmoc-Tyr(tBu)-OH, Fmoc-Gln(Trt)-OH, Fmoc-Leu-OH, Fmoc-Lys(Boc)-OH, Fmoc-His(Trt)-OH, Fmoc-Glu(OtBu)-OH, Fmoc-Val-OH, Fmoc-Cys(Trt)-OH as raw material, and DCC-HOBt as a condensing agent, a polypeptide resin was synthesized by a standard Fmoc solid-phase polypeptide synthetic process according to the amino acid sequence of linear sCT. The polypeptide was split from the resin by reacting at 0° C. for 1 h with 10 ml anhydrous HF as a splitting solution. The crude polypeptide obtained was dissolved in water, and lyophilized, to obtain 400 mg of a white dry powder. The crude polypeptide obtained was purified by RP-HPLC, and determined by Bio Mass Spectrometry to have a molecular weight of 3415.52, and a retention time of 11.9 min.

Step 2: Reaction of Polypeptide with a PEGylating Agent

[D-Ala$^1$,Cys$^7$,D-Ala$^{30}$]sCT, as purified by RP-HPLC, was dissolved in water, and adjusted with a phosphate buffer to pH=7-8, to which a suitable amount of mPEG$_{5000}$-MAL was added. Then, the system was reacted at room temperature, while monitoring the reaction process and the separated product by RP-HPLC. As analyzed by MALDI-TOF-MS, the product exhibited Mn=8550, a difference in molecular weights of two neighbouring peaks of 44, a typical structural feature of polyethylene glycol, and a retention time in RP-HPLC of 13.65 min.

EXAMPLE 2

Synthesis of [Val$^1$,Cys$^7$(mPEG$_{5000}$-MAL),Des-19, Ala$^{30}$]sCT (Compound 13)

The synthetic process was identical with that described in Example 1.

The peptide analogue obtained had a molecular weight of 3287.38, and a retention time of 8.13 min. As analyzed by MALDI-TOF-MS, the PEGylated product obtained exhibited Mn=8465, a difference in molecular weights of two neighbouring peaks of 44, a typical structural feature of polyethylene glycol, and a retention time in RP-HPLC of 13.16 min.

EXAMPLE 3

Synthesis of [Val$^1$, Ala$^7$, Cys$^{16}$(mPEG$_{5000}$-MAL), Des-19-22, Ala$^{30}$]sCT (Compound 14)

The synthetic process was identical with that described in Example 1.

The peptide analogue obtained had a molecular weight of 2896.12, and a retention time of 7.87 min. As analyzed by MALDI-TOF-MS, the PEGylated product obtained exhibited Mn=8292, a difference in molecular weights of two neighbouring peaks of 44, a typical structural feature of polyethylene glycol, and a retention time in RP-HPLC of 13.01 min.

EXAMPLE 4

Synthesis of [Val$^1$,Ala$^7$,Gln$^{11,18}$,Cys$^{16}$(mPEG$_{5000}$-MAL),Des-19-22,Ala$^{30}$]sCT (Compound 15)

The synthetic process was identical with that described in Example 1.

The peptide analogue obtained had a molecular weight of 2896.30, and a retention time of 8.56 min. As analyzed by MALDI-TOF-MS, the PEGylated product obtained exhibited Mn=8295, a difference in molecular weights of two neighbouring peaks of 44, a typical structural feature of polyethylene glycol, and a retention time in RP-HPLC of 13.26 min.

EXAMPLE 5

Synthesis of [Val$^1$, Cys$^7$(mPEG$_{5000}$-MAL),Des-19-22, Ala$^{30}$]sCT (Compound 16)

The synthetic process was identical with that described in Example 1.

The peptide analogue obtained had a molecular weight of 2937.33, and a retention time of 8.87 min. As analyzed by MALDI-TOF-MS, the PEGylated product obtained exhibited Mn=7907, a difference in molecular weights of two neighbouring peaks of 44, a typical structural feature of polyethylene glycol, and a retention time in RP-HPLC of 11.82 min.

EXAMPLE 6

Synthesis of [Val$^1$,Cys$^7$(mPEG$_{5000}$-MAL),Des-19, Ala$^{30}$]sCT (Compound 17)

The synthetic process was identical with that described in Example 1.

The peptide analogue obtained had a molecular weight of 3330.8, and a retention time of 10.66 min. As analyzed by MALDI-TOF-MS, the PEGylated product obtained exhibited Mn=8476, a difference in molecular weights of two neighbouring peaks of 44, a typical structural feature of polyethylene glycol, and a retention time in RP-HPLC of 13.38 min.

EXAMPLE 7

Synthesis of [Val$^1$,Cys$^7$(mPEG$_{5000}$-MAL), Gln$^{18}$, Des-19-22, Ala$^{30}$]sCT (Compound 18)

The synthetic process was identical with that described in Example 1.

The polypeptide compound obtained had a molecular weight of 2938.30, and a retention time of 9.54 min. As analyzed by MALDI-TOF-MS, the PEGylated product obtained exhibited Mn=8033, a difference in molecular weights of two neighbouring peaks of 44, a typical structural feature of polyethylene glycol, and a retention time in RP-HPLC of 11.10 min.

EXAMPLE 8

Synthesis of [Val$^1$,Cys$^7$(mPEG$_{5000}$-MAL), Gln$^{11}$, Des-19-22, Ala$^{30}$]sCT (Compound 19)

The synthetic process was identical with that described in Example 1.

The peptide analogue obtained had a molecular weight of 2938.23, and a retention time of 8.95 min. As analyzed by MALDI-TOF-MS, the PEGylated product obtained exhibited Mn=7899, a difference in molecular weights of two neighbouring peaks of 44, a typical structural feature of polyethylene glycol, and a retention time in RP-HPLC of 13.43 min.

EXAMPLE 9

Synthesis of [Val$^1$,Cys$^7$(mPEG$_{5000}$-MAL), Gln$^{11,18}$, Des-19-22,Ala$^{30}$]sCT (Compound 20)

The synthetic process was identical with that described in Example 1.

The peptide analogue obtained had a molecular weight of 2937.44, and a retention time of 9.47 min. As analyzed by MALDI-TOF-MS, the PEGylated product obtained exhibited Mn=8336, a difference in molecular weights of two neighbouring peaks of 44, a typical structural feature of polyethylene glycol, and a retention time in RP-HPLC of 13.69 min.

EXAMPLE 10

Synthesis of [Val$^1$, Ala$^7$, Cys$^{19}$(mPEG$_{5000}$-MAL), Des-20-22, Ala$^{30}$]sCT (Compound 21)

The synthetic process was identical with that described in Example 1.

The peptide analogue obtained had a molecular weight of 3008.48, and a retention time of 8.77 min. As analyzed by MALDI-TOF-MS, the PEGylated product obtained exhibited Mn=8055, a difference in molecular weights of two neighbouring peaks of 44, a typical structural feature of polyethylene glycol, and a retention time in RP-HPLC of 13.36 min.

EXAMPLE 11

Synthesis of [Val$^1$,Ala$^7$,Cys$^{19}$(mPEG$_{5000}$-MAL), Des-20-21, Ala$^{30}$]sCT (Compound 22)

The synthetic process was identical with that described in Example 1.

The peptide analogue obtained had a molecular weight of 3171.52, and a retention time of 9.46 min. As analyzed by MALDI-TOF-MS, the PEGylated product obtained exhibited Mn=8296, a difference in molecular weights of two neighbouring peaks of 44, a typical structural feature of polyethylene glycol, and a retention time in RP-HPLC of 13.53 min.

EXAMPLE 12

Evaluation on Calcium-Reducing Activity

The calcium-reducing activity of sCT(L)s and their PEGylated analogues was determined by administering them to abdomens of rats via subcutaneous injection, according to the method described in the literature (cf. Qian Deming, Shen Genquan, Ke Ruolun; Biological Assay of Calcitonin by Blood Calcium Determination in Rats, CHINESE JOURNAL OF PHARMACEUTICAL ANALYSIS, 1994, 14(3): 30-34).

The activity results as determined were listed as follows, while the reference activity of salmon calcitonin being 4500 IU/mg.

TABLE 1

The calcium-reducing activity results of linear sCT analogues and their PEGylated analogues

| Compound No. | Sequences | Activity (IU/mg) |
|---|---|---|
| 1 | [D-Ala$^1$,Cys$^7$,D-Ala$^{30}$]sCT | 5202 |
| 2 | [Val$^1$,Cys$^7$,Des-19,Ala$^{30}$]sCT | 1136 |
| 3 | [Val$^1$,Ala$^7$,Cys$^{16}$,Ala$^{30}$,Des-19-22]sCT | 3394 |
| 4 | [Val$^1$,Ala$^7$,Gln$^{11,18}$,Cys$^{16}$,Ala$^{30}$,Des-19-22]sCT | 807 |
| 5 | [Val$^1$,Cys$^7$,Des-19-22,Ala$^{30}$]sCT | 67 |
| 6 | [Val$^1$,Cys$^7$,Ala$^{30}$,Des-19]sCT | 4347 |
| 7 | [Val$^1$,Cys$^7$,Gln$^{18}$,Ala$^{30}$,Des-19-22]sCT | 233 |
| 8 | [Val$^1$,Cys$^7$,Gln$^{11}$,Ala$^{30}$,Des-19-22]sCT | 344 |
| 9 | [Val$^1$,Cys$^7$,Gln$^{11,18}$,Ala$^{30}$,Des-19-22]sCT | 920 |
| 10 | [Val$^1$,Ala$^7$,Cys$^{19}$,Ala$^{30}$,Des-20-22]sCT | 892 |
| 11 | [Val$^1$,Ala$^7$,Cys$^{19}$,Ala$^{30}$,Des-20-21]sCT | 379 |
| 12 | [D-Ala$^1$,Cys$^7$,(mPEG$_{5000}$-MAL),D-Ala$^{30}$]sCT | 1467 |
| 13 | [Val$^1$,Cys$^7$(mPEG$_{5000}$-MAL),Des-19,Ala$^{30}$]sCT | 438 |
| 14 | [Val$^1$,Ala$^7$,Cys$^{116}$(mPEG$_{5000}$-MAL),Des-19-22,Ala$^{30}$]sCT | 987 |
| 15 | [Val$^1$,Ala$^7$,Gln$^{11,18}$,Cys$^{16}$(mPEG$_{5000}$-MAL),Des-19-22,Ala$^{30}$]sCT | 301 |
| 16 | [Val$^1$,Cys$^7$(mPEG$_{5000}$-MAL),Des-19-22,Ala$^{30}$]sCT | 717 |
| 17 | [Val$^1$,Cys$^7$(mPEG$_{5000}$-MAL),Des-19,Ala$^{30}$]sCT | 1921 |
| 18 | [Val$^1$,Cys$^7$(mPEG$_{5000}$-MAL),Gln$^{18}$,Des-19-22,Ala$^{30}$]sCT | 763 |
| 19 | [Val$^1$,Cys$^7$(mPEG$_{5000}$-MAL),Gln$^{11}$,Des-19-22,Ala$^{30}$]sCT | 815 |
| 20 | [Val$^1$,Cys$^7$(mPEG$_{5000}$-MAL),Gln$^{11,18}$,Des-19-22,Ala$^{30}$]sCT | 1265 |
| 21 | [Val$^1$,Ala$^7$,Cys$^{19}$(mPEG$_{5000}$-MAL),Des-20-22,Ala$^{30}$]sCT | 1208 |
| 22 | [Val$^1$,Ala$^7$,Cys$^{19}$(mPEG$_{5000}$-MAL),Des-20-21,Ala$^{30}$]sCT | 1707 |

Compounds 1-11 in the Table were respectively non-PEGylated linear salmon calcitonin analogues as synthesized in Examples 1-11.

As can be seen from Table 1, linear salmon calcitonin analogues and their PEGylated analogues all exhibited an effective calcium-reducing activity.

EXAMPLE 13

Study on Long-Acting Performance of PEGylated sCT(L) Analogues

Compound 12 in Table 1 was taken as an example.

60 female Wistar rats, body weight 250-280 g, 16 weeks aged, were randomly divided into six groups: pseudo-castrated contrast group (10 rats); castrated contrast group (10 rats); calcitonin group (10 rats, twice every week, 0.036 µg/kg body weight/time); a low dose group of compound 12 (10 rats, twice every week, 0.216 µg/kg body weight/time); a high dose group of compound (10 rats, twice every week, 1.08 µg/kg body weight/time); and a high dose group of compound (10 rats, once every week, 1.08 µg/kg body weight/time). In each of the groups, the administration was given subcutaneously. During the experiment, the rats in each of the groups freely fed on standard solid forage and drank water. Except for the high dose group of compound 12 with administration once every week, blood samples were respectively taken from the orbits of the rats in other groups at the 6$^{th}$ week of administration, and subjected to the determination of osteocalcin, serum calcium and alkaline phosphatase (Table 2). At the end of the 12$^{th}$ week of administration, in addition to osteocalcin, serum calcium and alkaline phosphatase (Table 3), the bone densities of lumbar vertebrae, tibia and femur in the rats of each of the groups were determined (Table 4).

TABLE 2

Influence of calcitonin and its homologues on bone metabolism of rats at the 6$^{th}$ week of administration

| Group | Dose (µg/kg) | Alkaline phosphatase (u/100 ml) | Serum calcium (mg/100 ml) | Osteocalcin (ng/100 ml) |
|---|---|---|---|---|
| Pseudo-surgery group | — | 160.3 ± 19.0 | 10.7 ± 0.3 | 3.63 ± 0.51 |
| Model group | | 206.0 ± 25.2## | 10.4 ± 0.2 | 4.16 ± 0.25# |
| Calcitonin group | 0.036 | 179.8 ± 31.4* | 9.3 ± 0.2** | 3.90 ± 1.1* |
| Low dose group of compound 12 | 0.216 | 187.0 ± 30.4 | 9.8 ± 0.3** | 3.77 ± 0.25* |

TABLE 2-continued

Influence of calcitonin and its homologues on bone metabolism of rats at the 6$^{th}$ week of administration

| Group | Dose (μg/kg) | Alkaline phosphatase (u/100 ml) | Serum calcium (mg/100 ml) | Osteocalcin (ng/100 ml) |
|---|---|---|---|---|
| High dose group of compound 12 | 1.08 | 180.0 ± 19.4* | 9.2 ± 0.2** | 3.81 ± 0.24* |

Notes:
the administration was given subcutaneously twice every week; n = 10;
p < 0.05,
p < 0.01, as compared with the pseudo-surgery group;
*p < 0.05,
**p < 0.01, as compared with the model group.

TABLE 3

Influence of calcitonin and its homologues on bone metabolism of rats at the 12$^{th}$ week of administration

| Group | Dose (μg/kg) | Alkaline phosphatase (u/100 ml) | Serum calcium (mg/100 ml) | Osteocalcin (ng/100 ml) |
|---|---|---|---|---|
| Pseudo-surgery group | — | 161.4 ± 33.4 | 10.7 ± 0.3 | 3.33 ± 0.45 |
| Model group | | 215.6 ± 28.2## | 10.6 ± 0.4 | 4.10 ± 0.43# |
| Calcitonin group | 0.036 | 200.9 ± 40.1 | 9.3 ± 0.2** | 3.38 ± 0.17** |
| Low dose group of compound 12 | 0.216 | 202.4 ± 44.8 | 9.8 ± 0.3* | 4.01 ± 0.25 |
| High dose group of compound 12 | 1.08 | 188.2 ± 51.2 | 9.4 ± 0.4** | 3.95 ± 0.24 |

Notes:
the administration was given subcutaneously twice every week; n = 10;
p < 0.05,
p < 0.01, as compared with the pseudo-surgery group;
*p < 0.05,
**p < 0.01, as compared with the model group.

TABLE 4

Influence of calcitonin and its homologues on bone density of rats at the 12$^{th}$ week of administration

| Group | Dose (μg/kg) | Lumbar vertebrae (g/cm$^2$) | Femur (g/cm$^2$) | Tibia (g/cm$^2$) |
|---|---|---|---|---|
| Pseudo-surgery group | — | 0.189 ± 0.015 | 0.264 ± 0.003 | 0.256 ± 0.014 |
| Model group | | 0.168 ± 0.016## | 0.226 ± 0.013## | 0.242 ± 0.022 |
| Calcitonin group (twice/week) | 0.036 | 0.181 ± 0.013* | 0.242 ± 0.027 | 0.247 ± 0.127 |
| 101 Low dose group (twice/week) | 0.216 | 0.175 ± 0.021 | 0.240 ± 0.028 | 0.245 ± 0.014 |
| High dose group of compound 12 (twice/week) | 1.08 | 0.181 ± 0.018* | 0.241 ± 0.017 | 0.256 ± 0.017 |
| High dose group of compound 12 (once/week) | 1.08 | 0.182 ± 0.014* | 0.237 ± 0.0022 | 0.251 ± 0.015 |

Notes:
n = 10;
p < 0.01, as compared with the pseudo-surgery group;
*p < 0.05, as compared with the model group.

As can be seen from Tables 2, 3 and 4, at the 6$^{th}$ and 12$^{th}$ weeks of administration, high dose group of compound 12 was substantially equivalent to the positive contrast sCT group in the experiments relating to the influence on bone metabolism of rats. During a experiment relating to the influence on bone density lasted for 12 weeks, high dose group of compound 12 and the positive contrast sCT group both increased the bone density of lumbar vertebrae in the rats; in addition, the high dose group of PEGylated compound (administered once every week) exerted a substantially equivalent influence on the bone density of lumbar vertebrae as compared with the calcitonin (sCT) group (administered twice every week). The results exhibited the long-acting performance of PEGylated sCT(L).

The invention claimed is:

1. A linear salmon calcitonin analogue or the pharmaceutically acceptable salt thereof, which has the following structural features:

Aa$_1$-Ser-Asn-Leu-Ser-Thr-Aa$_2$-Aa$_3$-Leu-Gly-Aa$_4$-Leu-Ser-Gln-Glu-Aa$_5$-Aa$_6$-Aa$_7$-Aa$_8$-Pro-Aa$_9$-Thr-Asn-Thr-Gly-Ser-Aa$_{10}$-Thr-Pro-NH$_2$ (SEQ ID NO: 1)

wherein,
Aa$_1$ is selected from Cys, AcmCys, N-α-propinol-Cys, Ala, D-Ala, Val, Leu, Ile, Gly, Ser, Thr, Phe, Met, and Trp;
Aa$_2$ is selected from Cys, AcmCys, Ala, D-Ala, Val, Leu, Ile, Gly, Ser, Thr, Phe, Met, and Trp, wherein Aa$_1$ and Aa$_2$ are not both Cys;
Aa$_3$ is selected from Val, Gly, Met, Leu, Ile, Cys, Ala, and D-Ala;
Aa$_4$ is selected from Lys, Cys, Arg, and Gln;
Aa$_5$ is selected from Leu and Cys;
Aa$_6$ is selected from His, Cys, Lys, and Arg;
Aa$_7$ is selected from Lys, Arg, Cys, His, and Gln;
Aa$_8$ is selected from -Cys-Tyr- and Cys or is absent;
Aa$_9$ is selected from Arg, Lys, His, and Cys;
Aa$_{10}$ is selected from Ala and D-Ala;

unless especially specified, all of the amino acids are L-amino acids, and wherein at least one of Aa$_5$ and Aa$_8$ is Cys, and the Cys is unattached or is attached via its thiol group to a group selected from the group consisting of:

(a) PEG-M-, wherein
PEG is RO(CH$_2$CH$_2$O)$_n$—CH$_2$CH$_2$—, R=H or CH$_3$, n=25-2500; and

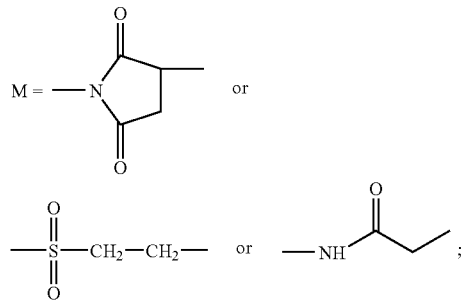

(b) [PEG-X—(CH$_2$)$_m$CO—NH]$_z$—, wherein
PEG is RO(CH$_2$CH$_2$O)$_n$—CH$_2$CH$_2$—, R=H or CH$_3$, n=25-2500;
X=O, NH or NHCO;
m=0-6; and
z=1; and (c) —[CO—X-PEG]$_z$, wherein
PEG is RO(CH$_2$CH$_2$O)$_n$—CH$_2$CH$_2$—, R=H or CH$_3$, n=25-2500;
X=O, NH or NHCO; and
z=1.

2. The linear salmon calcitonin analogue or the pharmaceutically acceptable salt thereof according to claim 1, wherein
Aa$_1$ is Cys, Ala, D-Ala, or Val;
Aa$_2$ is Cys, Ala, or D-Ala, wherein Aa$_1$ and Aa$_2$ are not both Cys;
Aa$_3$ is Val, Gly, Ala, or D-Ala;
Aa$_4$ is Lys or Arg;
Aa$_6$ is His or Arg;
Aa$_7$ is Lys or Arg; and
Aa$_9$ is Arg or His.

3. The linear salmon calcitonin analogue of the pharmaceutically acceptable salt thereof according to claim 2, wherein
Aa$_1$ is D-Ala or Val;
Aa$_2$ is Cys;
Aa$_3$ is Val or Gly;
Aa$_4$ is Lys;
Aa$_6$ is His;
Aa$_7$ is Lys;
Aa$_9$ is Arg.

4. The linear salmon calcitonin analogue or the pharmaceutically acceptable salt thereof according to any one of claims 1-3, wherein the PEG as a molecular weight ranging from 2,000 to 100,000.

5. The linear salmon calcitonin analogue or the pharmaceutically acceptable salt thereof according to claim 4, wherein the PEG has a molecular eight ranging from 5,000 to 60,000.

6. The linear salmon calcitonin analogue or the pharmaceutically acceptable salt thereof according to claim 5, which is selected from the group consisting of:

(1) Val-Ser-Asn-Leu-Ser-Thr-Ala-Val-Leu-Gly-Lys-Leu-Ser-Gln-Glu-Cys-His-Lys-Pro-Arg-Thr-Asn-Thr-Gly-Scr-Ala-Thr-Pro (SEQ ID NO:4);

(2) Val-Ser-Asn-Leu-Ser-Thr-Ala-Val-Leu-Gly-Lys-Leu-Ser-Gln-Glu-Cys(mPEG$_{5000}$-MAL)-His-Lys-Pro-Arg-Thr-Asn-Thr-Gly-Ser-Ala-Thr-Pro (SEQ ID NO:4);

(3) Val-Ser-Asn-Leu-Ser-Thr-Ala-Val-Leu-Gly-Gln-Leu-Ser-Gln-Glu-Cys-His-Gln-Pro-Arg-Thr-Asn-Thr-Gly-Ser-Ala-Thr-Pro (SEQ ID NO:5);

(4) Val-Ser-Asn-Leu-Ser-Thr-Ala-Val-Leu-Gly-Gln-Leu-Ser-Gln-Glu-Cys(mPEG$_{5000}$-MAL)-His-Gln-Pro-Arg-Thr-Asn-Thr-Gly-Ser-Ala-Thr-Pro (SEQ ID NO:5);

(5) Val-Ser-Asn-Leu-Ser-T hr-Ala-Val-Leu-Gly-Lys-Leu-Ser-Gln-Glu-Leu-His-Lys-Cvs-Pro-Arg-Thr-Asn-Thr-Gly-Ser-Ala-Thr-Pro (SEQ ID NO: 11);

(6) Val-Ser-Asn-Leu-Ser-Thr-Ala-Val-Leu-Gly-Lys-Leu-Ser-Gln-Glu-Leu-His-Lys-Cys(mPEG$_{5000}$-MAL)-Pro-Arg-Thr-Asn-Thr-Gly-Ser-Ala-Thr-Pro (SEQ ID NO: 11);

(7) Val-Ser-Asn-Leu-Ser-Thr-Ala-Val-Leu-Gly-Lys-Leu-Ser-Gln-Glu-Leu-His-Lys-Cys-Tyr-Pro-Arg-Thr-Asn-Thr-Gly-Ser-Ala-Thr-Pro (SEQ ID NO:12); and (8) Val-Ser-Asn-Leu-Ser-Thr-Ala-Val-Leu-Gly-Lys-Leu-Ser-Gln-Glu-Leu-His-Lys-Cys(mPEG$_{5000}$-MAL)-Tyr-Pro-Arg-Thr-Asn-Thr-Gly-Ser-Ala-Thr-Pro (SEQ ID NO:12).

7. A pharmaceutical composition, comprising the linear salmon calcitonin analogue or the pharmaceutically acceptable salt thereof according to any of claims 1, 2, 3, 4, 5, or 6, and pharmaceutically acceptable vehicles or excipients.

8. A method for the treatment of a disease associated with bone metabolism which comprises administering to a subject
   (i) the linear salmon calcitonin analogue or the pharmaceutically acceptable salt thereof according to any of claims 1, 2, 3, 4, 5, or 6 or
   (ii) the pharmaceutical composition according to claim 7, wherein the disease is selected from the group consisting of senile osteoporosis, postmenopausal osteoporosis, Paget's disease, hypercalcemia, bone pain caused by osteoporosis, and bone pain caused by bone tumor.

* * * * *